US009138600B2

(12) United States Patent
Batchelor et al.

(10) Patent No.: US 9,138,600 B2
(45) Date of Patent: Sep. 22, 2015

(54) ORAL CARE COMPOSITIONS COMPRISING A POLYMERIC DYE

(75) Inventors: Stephen Norman Batchelor, Wirral (GB); Andrew Joiner, Wirral (GB); Sheng Meng, Shanghai (CN); Carole Jane Philpotts, Wirral (GB); Qingsheng Tao, Shanghai (CN); Jinfang Wang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 177 days.

(21) Appl. No.: 13/378,264

(22) PCT Filed: Jun. 15, 2010

(86) PCT No.: PCT/EP2010/058366
§ 371 (c)(1),
(2), (4) Date: Dec. 14, 2011

(87) PCT Pub. No.: WO2010/149534
PCT Pub. Date: Dec. 29, 2010

(65) Prior Publication Data
US 2012/0093905 A1    Apr. 19, 2012

(30) Foreign Application Priority Data
Jun. 26, 2009   (EP) .................................... 09163936

(51) Int. Cl.
| A61K 8/02 | (2006.01) |
| A61Q 11/00 | (2006.01) |
| A61K 8/81 | (2006.01) |
| C09B 69/10 | (2006.01) |
| C11D 3/40 | (2006.01) |

(52) U.S. Cl.
CPC .............. A61Q 11/00 (2013.01); A61K 8/8152 (2013.01); A61K 8/8164 (2013.01); C09B 69/101 (2013.01); C09B 69/109 (2013.01); C11D 3/40 (2013.01); A61K 2800/57 (2013.01)

(58) Field of Classification Search
CPC .............................. C09B 69/101; A61Q 11/00
See application file for complete search history.

(56) References Cited

U.S. PATENT DOCUMENTS

| 3,277,119 | A | 10/1966 | Beyer et al. |
| 4,137,243 | A | 1/1979 | Farmer |
| 4,554,091 | A | 11/1985 | Jones et al. |
| 6,030,222 | A | 2/2000 | Tarver |
| 2005/0044644 | A1 | 3/2005 | Pearson et al. |
| 2005/0175552 | A1 | 8/2005 | Hoic et al. |
| 2006/0104922 | A1 | 5/2006 | Tarver et al. |
| 2006/0183658 | A1* | 8/2006 | Sadlowski et al. ............ 510/392 |
| 2008/0152599 | A1* | 6/2008 | Brignoli et al. ................ 424/49 |
| 2008/0152600 | A1 | 6/2008 | Huang et al. |
| 2010/0136067 | A1* | 6/2010 | Butler et al. .................. 424/401 |

FOREIGN PATENT DOCUMENTS

| EP | 0799864 A1 | 10/1997 |
| EP | 1935395 A1 | 6/2008 |
| EP | 2308932 A1 | 4/2011 |
| GB | 567716 | 2/1945 |
| WO | WO0125341 A1 | 4/2001 |
| WO | WO03006561 A2 | 1/2003 |
| WO | WO2006055787 A1 | 5/2006 |
| WO | WO2006055843 A2 | 5/2006 |
| WO | WO2007087252 A1 | 8/2007 |
| WO | WO2008009579 A1 | 1/2008 |
| WO | WO2008091524 A1 | 7/2008 |
| WO | WO2008100445 A2 | 8/2008 |
| WO | WO2009030614 A1 | 3/2009 |
| WO | WO2010089059 A1 | 8/2010 |
| WO | WO2010102861 A1 | 9/2010 |

OTHER PUBLICATIONS

Rhodamine B, Sigma-Aldrich, 3 pages, 2014.*
Pigment Blue 1, Dyestuffintermediates, 6 pages, 2012.*
Asquith et al., Self-coloured Polymers based on Anthraquinone Residues, JSDC, 1977, vol. 93, 114-125.
Yu et al., Functionalization of Poly(methyl acrylate). 1. Neighboring-Group Effects int eh REactions with Various Amines, Macromolecules, 1994, vol. 27, 7121-7126.
International Search Report PCT/EP2010/058366 dated Oct. 14, 2011.

* cited by examiner

*Primary Examiner* — Kyle Purdy
(74) *Attorney, Agent, or Firm* — Greenberg Traurig, LLP

(57) ABSTRACT

An oral care composition comprising a dye polymer, for modifying the color of teeth.

4 Claims, No Drawings

ORAL CARE COMPOSITIONS COMPRISING A POLYMERIC DYE

The present invention relates to oral care compositions for modifying the colour of teeth, in particular for enhancing the white appearance of teeth.

Certain tooth whitening compositions are already known.

U.S. Pat. No. 6,030,222 (Tarver) discloses a whitening composition comprising a dye that, when absorbed by a tooth, causes the tooth to reflect a color of light which is whiter than the initial color of light reflected by the tooth.

US 2006/0104922 (Tarver) discloses a tooth whitening system for concealing tooth discoloration. The system comprises a single, spectrally pure, substantially violet dye and a carrier for applying it to the teeth.

EP 1,935,395 (Brignoli and Joiner) discloses a tooth whitening system comprising a pigment and a soluble deposition aid for said pigment.

Certain other publications describe the use of polymeric dyes, largely for dyeing textiles or hair.

WO 06/055787 (Proctor and Gamble), describes dyes attached to cellulose ether in laundry formulations. The polymeric dyes are claimed to work effectively on cellulosic garments.

WO 06/055843, WO 07/087,252, WO 08/091,524, and WO 08/100,445 (all Milliken) describe dyes linked to polyether groups, for use in laundry formulations. The colour change benefit is found predominately on cellulosic garments.

U.S. Pat. No. 4,137,243 (Milliken) discloses polymeric anthraquinone derived colorants and their use in textile production and/or finishing.

WO 08/009,579 (Ciba) discloses polymer chains with pendant cationic charged dyes for use in hair dyeing.

WO 09/030,614 (Ciba) discloses personal care compositions comprising dye-polymer complexes.

The object of the invention is to provide a product for modifying the colour of teeth, in particular for increasing the apparent whiteness of teeth.

In a first aspect of the present invention, there is provided an oral care composition comprising a dye polymer, for modifying the colour of teeth.

In a second aspect of the present invention, there is provided the use of a dye polymer, for the manufacture of an oral care composition for modifying the colour of teeth.

In a third aspect of the present invention, there is provided an oral care composition comprising a dye polymer in which the dye functionality is covalently attached to the remainder of the polymer.

In a fourth aspect of the present invention, there is provided a method of modifying the colour of teeth, said method comprising the application of an oral care composition comprising a dye polymer.

The inventors have found that excellent tooth whitening may be obtained by use of the present invention with dye polymers of appropriate colour (vide infra). It is believed that the dye polymers used in the present invention deposit with relatively high efficiency onto the surface of the teeth, thereby enhancing their effectiveness. An associated benefit is that dye polymers are much less likely to need deposition aids than simple dyes or pigments.

The application of the oral care composition is to the teeth, typically directly to the teeth, for example by use a toothpaste, mouthwash, or leave-on treatment. Most typically, the oral care composition is a toothpaste and is applied using a toothbrush.

The colour to which the teeth are modified depends upon the colour of the dye polymer used. In preferred embodiments, the dye polymer leads to whitening of the teeth. This may be achieved by use of a dye polymer that has a blue or violet colour. Dye polymers of this type have a hue angle in the CIELAB system of from 220 to 320 degrees, more preferably between 250 and 290 degrees, when deposited on human teeth. A detailed description of hue angle may be found on p57 of Colour Chemistry 3rd edition by H. Zollinger published by Wiley-VCH.

The maximum absorption for the dye polymer in the range from 400 to 700 nm is termed $\lambda_{max}$. Preferably, the dye polymer has a $\lambda_{max}$ of from 500 to 580 nm, more preferably from 520 to 560 nm.

The wavelength of the maximum light absorption for the dye polymer in the range from 400 to 700 nm is termed $\lambda_{max}$. Preferably, the dye polymer has a $\lambda_{max}$ of from 500 to 650 nm, more preferably from 535 to 590 nm.

The absorbance value for the dye polymer at its $\lambda_{max}$ is preferably at least 0.01 and more preferably at least 0.2. Absorption values are measured on 1% aqueous solutions, optionally with 0.1% by weight linear alkylbenzenesulphonate present, in 1 cm cells.

The preferred whitening effect is achieved by the dye polymer depositing on the teeth and leading to sufficient light being reflected from the teeth for them to be perceived as whiter.

The preferred colour of the dye polymer is typically achieved by incorporation of dye moieties having blue or violet colour, i.e. having a hue angle of from 220 to 320 degrees, more preferably between 250 and 290 degrees. Alternatively, however, the colour may be achieved through incorporation of a mixture of dye moieties having hue angles outside of the preferred range, for example by mixing red and green-blue dye moieties in a given dye polymer.

In a further alternative embodiment, whitening of the teeth may be achieved through application of a mixture of dye polymers having hue angles outside of the preferred range; for example, red and green-blue dye polymers.

The dye moieties in the dye polymer are preferably selected from the following chromophore classes: anthraquinone, azo, triphenyl methane, azine, xanthene, indigoid, methane, and phthalocyanine; they are more preferably selected from anthraquinone, azo, triphenyl methane, xanthene and indigoid. Dye polymers comprising anthraquinone dye moieties are particularly preferred, especially those devoid of charged groups or have one or two sulphonate ($SO_3^-$) groups covalently bound to them.

The dye polymer typically has a number average molecular weight in the range from 1000 to 500000, preferably from 2500 to 250000, more preferably 5000 to 50000. The number average molecular weight is the ordinary arithmetic mean of the molecular weights of the individual macromolecules. It is determined by measuring the molecular weight of x polymer molecules, summing the weights, and dividing by x. Molecular weights may be determined by Gel Permeation Chromatography.

Preferred dye polymers for modifying the colour of teeth have the dye functionality covalently attached to the remainder of the polymer. Particularly preferred dye polymers are of the form:

(Polymer chain)-(Y-dye)$_x$ wherein Y is a link between the dye and the polymer chain and x is the number of dye moieties associated with a given polymer molecule. Y is typically an organic bridging group covalently connecting an aromatic ring of the dye to the polymer chain. Preferably, Y is from 1 to 8 atoms, more preferably 3 to 6 atoms; the atoms being selected from: C, N, O, and S. The polymer chain may also be directly connected to the dye and in this case Y is a covalent bond.

Y may be selected from: —C(O)N(R)—, —N(R)C(O)—, —C(O)OR'—, —N(R)—, —O—, —S—, —S(O$_2$)—, —S(O$_2$)N(R)—, —N(COR)—, and —N(SO$_2$R)—, wherein R is selected from H, C1-C6 branched or linear alkyl, phenyl, and benzyl groups and R' is an alkylene group. Most preferably, the organic bridging group is —N(R)C(O)—, and R is most preferably H or Me.

The ratio of dye moieties to polymerized monomer units in the polymer chain of the dye polymer may be critical to its effectiveness. This ratio may be as low as 1:10,000, but is typically at least 1:100 and is preferably at least 1:50. Preferably, the ratio is no greater than 1:3, more preferably no greater than 1:5 and most preferably no greater than 1:7.

Throughout this specification, a dye moiety should be understood to be an individual dye functionality. Such moieties are typically associated with a single polymerized monomer unit in the polymer chain.

The dye polymer may be obtained by the addition of dye moieties to a preformed polymer or by a polymerisation reaction involving a monomer comprising a dye moiety. Dye polymers obtained by the former method are preferred. Dye polymers obtained by the latter method are typically copolymers of the monomer comprising the dye moiety and one or more monomers not comprising dye moieties.

The addition of dye moieties to a preformed polymer may be done using reactive dyes, which carry reactive groups which may react with OH, SH or NH$_2$ groups on the preformed polymer. Examples of such dye moieties are listed as reactive dye in the colour index, for example reactive blue 19, reactive blue 2, reactive blue 4, reactive blue 6, reactive blue 7, reactive blue 11 and reactive blue 12. To achieve the optimum shade it is preferable to combine a reactive blue with a reactive orange dye or a reactive red dye on the polymer. Examples of these dyes are reactive red 1, reactive red 2, reactive red 9, reactive orange 13, reactive orange 16. Preferably the molar ratio of the reactive blue to the reactive red or reactive orange dye is from 2:1 to 10:1. Metal complexed azo reactive dyes are preferably not used.

Preferably, groups on a "reactive" preformed polymers may be reacted with OH, SH or NH$_2$ groups on the dye moiety, most typically an NH$_2$ group. Examples of reactive groups of preformed polymers are anhydride, N-hydroxysuccinimide, isocyanate, azide, alkyne, oxazolone, epoxide, aldehyde, ketone, acrylate, pyridyldisulfide, thiazolidine-2-thione, pentafluorophenol ester, 2,4,5-trichlorophenol ester and endo-N-hydroxy-5-norbornene-2,3-dicarboxylmide. Preformed polymers suitable for addition of dye moieties include polyvinylalcohol; copolymers of maleic anhydride, such as methyl vinylether/maleic anhydride copolymer; copolymers of methacrylic anhydride; cellulose and derivatives thereof such as cellulose ether, ethyl cellulose, methyl cellulose, carboxymethyl cellulose, hydroxylpropyl methylcellulose, hydroxylpropyl cellulose, hydroxylethyl cellulose, dialdehyde cellulose; chitin; chitosan; starch; dialdehyde starch; dextran; dialdehyde dextran; polylysine; alginate; guar bean gum; locust bean gum; xanthan; gelatine; pectin; haluronic acid; poly(allylamine); poly(vinyl amine); poly(ethylenimine); poly(acrylic acid) and copolymers of acrylic acid, poly(methacrylic acid) and copolymers of methacrylic acid; poly(N-acryloxysuccinimide) and copolymers of N-acryloxysuccinimide; poly(N-methacryloxysuccinimide) and copolymers of N-methacryloxysuccinimide; poly(p-styrenesulfonate sodium) and co-polymers of p-styrene-sulfonate sodium; poly(2-acrylamido-2-methyl-1-propanesulfonic acid) and copolymers of 2-acrylamido-2-methyl-1-propanesulfonic acid; poly(2-hydroxyethyl acrylate) and co-polymers of 2-hydroxyethyl acrylate; poly(2-hydroxyethyl methacrylate) and copolymers of 2-hydroxyethyl methacrylate; poly(2-glycidyl acrylate) and copolymers of 2-glycidyl acrylate; poly(2-glycidyl methacrylate) and copolymers of 2-glycidyl methacrylate; poly(4-epoxystyrene) and copolymers of 4-epoxystyrene; poly(methallyl isothiocyanate) and copolymers of methallyl isothiocyanate, poly(2-vinyl-4,4-dimethyl-5-oxazolone) and copolymers of 2-vinyl-4,4-dimethyl-5-oxazolone; poly(γ-acryloyloxy-ϵ-caprolactone) and copolymers of γ-acryloyloxy-ϵ-caprolactone; poly(3-(3-methacrylamidopropanoyl)thiazolidine-2-thione and copolymers of 3-(3-methacrylamidopropanoyl) thiazolidine-2-thione; poly(vinyl isocyanate) and copolymers of vinyl isocyanate; poly(1-methyl-vinylisocyanate) and copolymers of 1-methyl-vinylisocyanate, poly(4-vinyl benzaldehyde) and copolymers of 4-vinyl benzaldehyde.

Post-polymerization modification methods for reactive polymers are described in detail in Gauthier, M. A., Gibson, M. I., and Klok H-A., *Angew. Chem. Int. Ed* 2009 48, 48058. Functional groups of reactive polymers include anhydride, N-hydroxysuccinimide, isocyanate, azide, alkyne, oxazolone, epoxide, aldehyde, ketone, acrylate, pyridyldisulfide, 2,4,5-trichlorophenol ester, thiazolidine-2-thione, pentafluorophenol ester, and endo-N-hydroxy-5-norbornene-2,3-dicarboxyimide.

For dye polymers prepared by reaction with a reactive polymer, the dye moiety preferably comes from organic dyes selected from the following chromophore classes: anthraquinone, azo, azine, triphenodioxazine, triphenyl methane, xanthene and phthalocyanin, more preferably azo, anthraquinone and azine chromophore classes. The dye must contain an OH, SH or NH$_2$ group in order to react with the reactive polymer. Preferably the dye contains an NH$_2$ group and more preferably the NH$_2$ group is directly bonded to an aromatic ring.

Dyes are described in Industrial Dyes (K. Hunger ed, Wiley VCH 2003, ISBN 3-527-30426-6). Named dyes are those as found in the Color Index; ©2009 Society of Dyers and Colourists and American Association of Textile Chemists and Colorists.

Preferred dyes for such reactions are acid violet 1, acid violet 3, acid violet 6, acid violet 11, acid violet 13, acid violet 14, acid violet 19, acid violet 20, acid violet 36, acid violet 36:1, acid violet 41, acid violet 42, acid violet 43, acid violet 50, acid violet 51, acid violet 63, acid violet 48, acid blue 25, acid blue 40, acid blue 40:1, acid blue 41, acid blue 45, acid blue 47, acid blue 49, acid blue 51, acid blue 53, acid blue 56, acid blue 61, acid blue 61:1, acid blue 62, acid blue 69, acid blue 78, acid blue 81:1, acid blue 92, acid blue 96, acid blue 108, acid blue 111, acid blue 215, acid blue 230, acid blue 277, acid blue 344, acid blue 117, acid blue 124, acid blue 129, acid blue 129:1, acid blue 138, acid blue 145, direct violet 99, direct violet 5, direct violet 72, direct violet 16, direct violet 78, direct violet 77, direct violet 83, food black 2, direct blue 33, direct blue 41, direct blue 22, direct blue 71, direct blue 72, direct blue 74, direct blue 75, direct blue 82, direct blue 96, direct blue 110, direct blue 111, direct blue 120, direct blue 120:1, direct blue 121, direct blue 122, direct blue 123, direct blue 124, direct blue 126, direct blue 127, direct blue 128, direct blue 129, direct blue 130, direct blue 132, direct blue 133, direct blue 135, direct blue 138, direct blue 140, direct blue 145, direct blue 148, direct blue 149, direct blue 159, direct blue 162, direct blue 163, food black 2, food black 1 where the acid amide group (NHCOCH$_3$) is replaced by NH$_2$, disperse blue 5, disperse blue 6, disperse blue 9, disperse blue 19, disperse blue 28, disperse blue 4, disperse blue 56, disperse blue 60, disperse blue 81, disperse violet 1, disperse violet 4, disperse violet 8, Basic Violet 2, Basic Violet 5, Basic Violet 12, Basic Violet 14, Basic Violet 8, Basic Blue 12, Basic Blue 16, Basic Blue 17, Basic Blue 47 and Basic Blue 99.

Dye polymers prepared from reactive polymers are preferably prepared by addition of an organic dye to active ester groups on the preformed polymer or, preferably, by addition to anhydride, isocyanate, axazolone, or epoxide groups on the preformed polymer.

A preferred dye polymer may be prepared by addition of an amine-substituted dye to an anhydride-containing preformed polymer. An example of such a reaction may be represented thus:

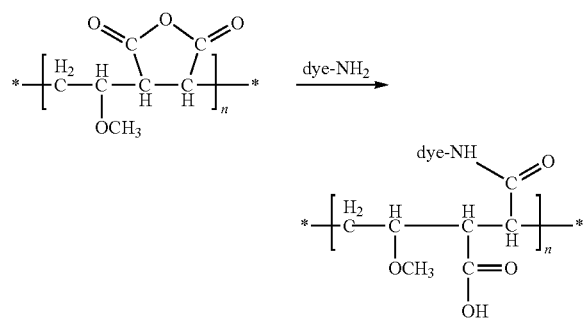

When the dye polymer is prepared by a polymerisation reaction involving a monomer comprising a dye moiety (i.e. a "dye monomer"), the dye monomer may be of the form:

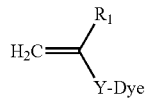

wherein Y is an organic bridging group covalently connecting a dye to the alkene moiety of the dye monomer and R$_1$ is selected from: alkyl; aryl; halogen; ester; acid amide; and CN, and is most preferably H or CH$_3$.

Suitable dye monomers may be prepared by acylation of an NH$_2$ group, preferably an NH$_2$ group directly bonded to an aromatic ring of the dye monomer. Suitable dye-NH$_2$ compounds are the same as those listed above as suitable for post-polymerization modification of reactive polymers. Particularly preferred dye monomers are food black 2, food black 1 where the acid amide group (NHCOCH$_3$) is replaced by NH$_2$ anthraquinone disperse dyes, and anthraquinone acid dyes.

Preferably the dye monomer is of the form:

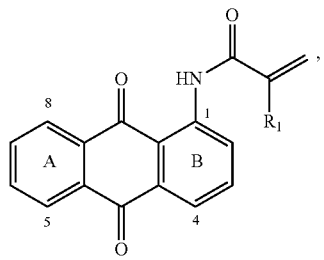

wherein R$_1$ is as previously defined and the A and B ring are further substituted. Preferred substituent groups include NH$_2$, NHAr, NHR$_5$, NR$_5$R$_6$, OH, Cl, Br, CN, OAr, NO$_2$, SO$_2$OAr, SO$_3$Na, CH$_3$ and NHCOC(R1)=CH$_2$, wherein R$_5$ and R$_6$ are independently selected from C1-C8 branched, cyclic or linear alkyl which may be substituted by OH, OMe, Cl or CN. More preferably the dye monomer is substituted at the 4, 5 or 8 position by at least one groups selected from NH$_2$, NHAr, and NHR$_5$, NR$_5$R$_6$. Most preferably, when present OH and NO$_2$ groups are at 4, 5 or 8 position and no more than two NO$_2$ groups are present.

Preferably the dye monomer is prepared by addition of an acrylate or methacrylate functionality to a dye selected from: disperse blue 1; disperse blue 5; disperse blue 6; disperse blue 9; disperse blue 19; disperse blue 28; disperse blue 40; disperse blue 56; disperse blue 60; disperse blue 81; disperse violet 1; disperse violet 4, disperse violet 8 acid blue 25, acid blue 62, acid blue 25, acid blue 23, acid blue 40, acid blue 41, acid blue 43, acid blue 53, acid blue 56, acid blue 62, acid blue 69, acid blue 78, acid blue 45, acid blue 47, acid blue 49, acid blue 51, acid blue 81:1, acid violet 51, acid violet 63, acid violet 36, acid violet 36:1, food black 2 and food black 1 where the acid amide group (NHCOCH$_3$) is replaced by NH$_2$.

Synthesis of a variety of dye monomers is discussed in U.S. Pat. No. 4,943,617 (BASF), U.S. Pat. No. 5,055,602 (Bausch and Lomb), WO2005/021663 (Eastman), and U.S. Pat. No. 5,362,812 (3M).

The dye monomer is typically copolymerised with monomers not comprising a dye moiety (vide supra). Preferred co-monomers of this type are:

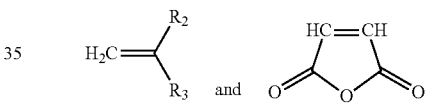

wherein R$_2$ and R$_3$ are independently selected from: H; C1-C8 branched, cyclic, or linear alkyl or alkyloxy chains; C(O)OR$_4$ or C(O)N(R$_4$)$_2$, wherein R$_4$ is independently H or a C1-C8 branched or linear alkyl chain, preferably H or a C1-C4 linear alkyl chain; heteroaromatic; phenyl; benzyl; polyether; cyano; Cl; or F. Preferably R$_2$ and R$_3$ are independently selected from NHCOCH$_3$, CH$_3$, C$_2$H$_5$, OH, CH$_3$O, C$_2$H$_5$O, amine, Cl, F, Br, I, NO$_2$, CH$_3$SO$_2$, and CN.

Monomers not comprising a dye moiety that are suitable for co-polymerisation with dye monomers to give a dye polymer are dimethylaminoethyl methacrylate (DMAEMA) (preferred), methyl methacrylate, methyl acrylate, hydroxyethyl methacrylate (preferred), ethyl methacrylate, ethyl acrylate, hydroxyethyl acrylate (preferred), butyl methacrylate, butyl acrylate, acrylamide (preferred), t-butyl methacrylate, t-butyl acrylate, sodium 4-vinylbenzenesulphonate (preferred), styrene, benzyl methacrylate, acrylic acid (preferred), vinyl acetate, vinyl pyridine, sodium acrylate (preferred), diethylaminoethyl methacrylate (preferred), 4-vinylphenol, methacrylic acid (preferred), acrylonitrile, 4-vinyl-9H-carbazole, sodium methacrylate (preferred), 4,4-dimethyl-2-vinyloxazol-5(4H)-one, 4,4-dimethyl-2-(prop-1-en-2-yl)oxazol-5 (4H)-one, vinyl pyrrolidone (preferred), 4-pentenoic acid, glycidyl methacrylate, maleic anhydride (preferred), ethyl 2-cyanoacrylate, stearyl acrylate, glycosyloxyethyl methacrylate, di(ethylene glycol) methyl ether methacrylate, poly (ethylene glycol) ethyl ether methacrylate, poly(ethylene glycol) methyl ether methacrylate, isopropyl methacrylate, 2-hydroxypropyl methacrylate, 2-isocyanatoethyl methacrylate, 2-(methylthio)ethyl methacrylate, 2-aminoethyl methacrylate hydrochloride (preferred), furfuryl methacrylate, cyclohexyl methacrylate, 2,2,2-trifluoroethyl methacrylate, tetrahydrofurfuryl methacrylate, hexyl methacrylate, 3-chloro-2-hydroxypropyl methacrylate, N-isopropylacrylamide (preferred), N,N-dimethylacrylamide (preferred), 2-ethylhexyl methacrylate, 2-(dimethylamino)ethyl methacrylamide (preferred), potassium 3-sulphopropyl methacrylate (preferred), potassium 5-methyl-4-oxohex-5-ene-1-sulphonate, 2-butoxyethyl methacrylate, 2-(t-butylamino)ethyl methacrylate, 2-acrylamido-2-methyl-1-propanesulphonic acid, 4-vinylbenzoic acid (preferred), N-(6-aminopyridin-2-yl)acrylamide, N-(3-aminophenyl) acrylamide, 2-acrylamido pyridine, 4-vinylphenylboronic acid, itaconic acid (preferred), 2-aminoethyl methacrylate, and methylvinyl ether.

Mixtures of monomers not comprising a dye moiety may be used in the co-polymerisation reaction. Of such monomers, it is preferably that at least 50%, and more preferably at least 80%, by weight are selected from monomers that have a molecular weight of less than 300 and contains an amine, amide, OH, $OCH_3$, $SO_3^-$ or $COO^-$ group. Dye polymers made of such monomer blends tend to have better water solubility.

In this specification DAQ is 1,4-diaminoanthraquinone; $AB_{25}$ is Acid Blue 25; MV3RAX is Methylene Violet 3RAX; and MVE/MA is methylvinylether/maleic anhydride co-polymer.

Particular examples of polymers of the current invention are the addition co-polymers of DMAEMA and DAQ acrylate, DMAEMA and $AB_{25}$ acrylate, DMAEMA and MV3RAX acrylate; and reactive polymer adducts of MVE/MA and DAQ, MVE/MA and $AB_{25}$, MVE/MA and MV3RX, and MVE/MA and Food Black 2. The specified reactive polymer adducts may be considered to comprise dye-maleate monomer units.

The dye polymer is preferably water soluble, this property enhancing its formulation and delivery to the tooth surface. Water solubility should be understood as being at 25° C. and the water solubility of the dye polymer is preferably at least 0.01 g/l, more preferably at least 0.1 g/l and most preferably at least 1 g/l. Being water soluble at 25° C. typically means that the dye polymer tends to stay in solution in the mouth, where the temperature can be somewhat hotter, rising to up to 37° C. It should be understood that the water solubility of the dye polymer is at its natural pH, although it also beneficial that the dye polymer is water soluble at pH 8 and/or pH 9, because of the alkaline environment typically found in the mouth.

The dye polymer may be substituted by negative or positively charged groups such as $SO_3^-$, $CO_2^-$ or quaternary nitrogen. Such charged groups can enhance the water solubility of the dye polymer. Preferably the dye polymer does not contain quaternary nitrogen groups.

The amount of dye polymer in the composition is preferably from 0.001 to 2%, more preferably from 0.02 to 1%, and most preferably from 0.05 to 0.5% by weight.

The dye polymer may be uniformly spread throughout the composition or, in certain preferred embodiments, it may be dispersed in a second phase such as a stripe or other co-extruded second phase. Such preferred "dual phase" compositions have the advantage that the phases may be differently coloured, presenting a more visually attractive product to the consumer.

The oral care compositions of the invention may comprise other components in accordance with their nature.

Preferably, the oral care composition comprises water, thickener, surfactant, and abrasive. Suitable thickeners include silicas and calcium carbonate. The preferred thickener is silica. Suitable surfactants include the alkali-metal alkyl sulphate surfactants such as the sodium alkyl sulphates, the most preferred being sodium laurylsulphate.

Preferred abrasive materials include silicas, aluminas, calcium carbonates, dicalcium phosphates, calcium pyrophosphates, hydroxyapatites, trimetaphosphates, insoluble hexametaphosphates and so on, including agglomerated particulate abrasive materials, usually in amounts between 3 and 60% by weight of the oral care composition. The most preferred abrasives are calcium carbonate and silica, especially silica.

The oral care composition according to the invention may comprise a plurality of visually distinct formulations. By this is meant that the composition comprises separate and different formulations which are adjacent one another when extruded from a tube or the like. Typical examples include a composition which comprises a stripe formulation and a base formulation. Another example includes a composition comprising a core formulation and a sheath formulation. The core formulation is preferably located coaxially within the sheath formulation. The term 'coaxially' means substantially central in cross section and is not meant to represent any mathematical accuracy.

Preferably, the oral care composition comprising more than one formulation as described in the previous paragraph comprises at least 90%, preferably at least 95%, and most preferably at least 99% by weight of the total dye polymer in one of the formulations.

Where the composition comprises more than one formulation and where one of the formulations comprises the bulk of the dye polymer as described, the remaining formulation(s) is/are preferably translucent or visually clear.

Preferably, the oral care composition comprises a first formulation located co-axially within a second formulation, the first formulation comprising the dye polymer. In such an oral care composition, the second formulation preferably comprises a pearlescer, such as mica.

The oral care compositions according to the invention may comprise further ingredients which are common in the art, such as:

antimicrobial agents, e.g. Triclosan, chlorhexidine, copper, zinc, and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds, such as 2,2' methylenebis-(4-chloro-6-bromophenol);

anti-inflammatory agents such as ibuprofen, flurbiprofen, aspirin, indomethacin etc.;

anti-caries agents such as sodium- and stannous fluoride, aminefluorides, sodium monofluorophosphate, sodium trimeta phosphate and casein;

plaque buffers such as urea, calcium lactate, calcium glycerophosphate and strontium polyacrylates;

vitamins such as Vitamins A, C and E;

plant extracts;

desensitising agents, e.g. potassium citrate, potassium chloride, potassium tartrate, potassium bicarbonate, potassium oxalate, potassium nitrate and strontium salts;

anti-calculus agents, e.g. alkali-metal pyrophosphates, hypophosphite-containing polymers, organic phosphonates and phosphocitrates etc.;

biomolecules, e.g. bacteriocins, antibodies, enzymes, etc.;

flavours, e.g. peppermint and spearmint oils;

proteinaceous materials such as collagen;

preservatives;
opacifying agents;
colouring agents;
pH-adjusting agents;
sweetening agents;
pharmaceutically acceptable carriers, e.g. starch, sucrose, water or water/alcohol systems etc.;
humectants such as glycerol, sorbitol, propyleneglycol, xylitol, lactitol etc.;
binders and thickeners such as sodium carboxymethyl-cellulose, xanthan gum, gum arabic etc. as well as synthetic polymers such as polyacrylates and carboxyvinyl polymers such as Carbopol®;
buffers and salts to buffer the pH and ionic strength of the oral care composition; and
other optional ingredients that may be included are e.g. bleaching agents such as peroxy compounds e.g. potassium peroxydiphosphate, effervescing systems such as sodium bicarbonate/citric acid systems, colour change systems, and so on.

The oral care compositions may be in any form common in the art, e.g. toothpaste, gel, mousse, aerosol, chewing gum, lozenge, powder, cream, and may also be formulated into systems for use in dual-compartment type dispensers. Preferred forms are toothpastes and chewing gums. Preferred chewing gum compositions are sugar free.

In the following non-limiting examples, amounts are percentages by weight unless otherwise stated.

EXAMPLES

Example 1

Addition of Dye Moieties to a Preformed Polymer 1,4-Diaminoanthraquinone (DAQ) (90% technical grade) and poly(methyl vinyl ether-alt-maleic anhydride) (PMVEMA, CAS: 9011-16-9, Mn=80000, Mw=210000) were obtained from Aldrich and used as received. 2.044 g of PMVEMA (0.013 mol maleic anhydride) and 40 ml dry THF was charged into a 100 ml three-necked round bottle equipped with a condenser and a magnetic stirring bar. The mixture was purged with $N_2$ stream and stirred at 40° C. for 15 min. Then 0.284 g DAQ (0.0012 mol) dissolved in 20 ml THF was added slowly into the reactor and the reaction carried out at 40° C. for 2.5 hours. Cooled reaction mixture was poured into 500 mL petroleum ether for precipitation. The resultant polymer was further washed by $CHCl_3$ for three times to remove the non-reacted dyes and vacuum dried at room temperature over night thereafter. Finally, remaining non-reacted maleic anhydride units in the resultant polymer were hydrolysed using methods known in the art to yield the final dye polymer: DP1.

The above polymerisation reaction was repeated using ratio's of dye to PMVEMA of 0.6:99.4, 2.4:97.6, 4.8:95.2, and 9.6:90.4 by weight respectively, these polymers being coded PP1, PP2, PP3 and PP4 respectively.

Example 2

Polymerisation Reactions Involving a Dye Monomer

In a first stage, a dye monomer was prepared by the reaction of DAQ (90% technical grade, ex Aldrich) and acryloyl chloride in the presence of sodium dicarbonate. (Methacryloyl chloride[2-methylprop-2-enoyl chloride] also functions well to provide an analogous dye monomer). A mixture of 150 ml anhydrous THF, 1 g DAQ and 0.6 g sodium dicarbonate was charged into 250 ml three-necked round bottom flask equipped with a condenser, a dropping funnel, and a magnetic stirring bar. The flask was then maintained at room temperature while 0.38 g acryloyl chloride dissolved in 5 ml anhydrous THF was added from the dropping funnel over 3 hours. The reaction mixture was stirred at 25° C. for another 20 hours. The reaction mixture was then filtered to remove the insoluble solids and the clear solution was dried by using rotary evaporation. The resulting violet powder was washed with water three times and the powder dried under vacuum at 60° C. for 24 hours. The structure of the DAQ-acrylate dye monomer was confirmed using NMR and showed that the reaction had gone to greater than 88% completion. Consequently greater than 88% of the anthraquinone contained one —NHCOCH=$CH_2$ group.

In a second (polymerisation) stage, a solution of 3 g dimethylaminoethyl methacrylate (DMAEMA), 0.03 g of the DAQ-acrylate dye monomer as prepared above and 0.06 g AIBN in 10 ml toluene was charged into a dry $N_2$ gas purged two-necked tube with a condenser and a magnetic stirring bar. The tube was sealed and placed in a regulated thermostat bath at 65° C. for 24 hours. The solution was precipitated in five-fold excess of petroleum ether for three times after the reaction, followed by drying under vacuum at 40° C. for 24 hour to give the resulting dye polymer: DP2.

The above polymerisation reaction was repeated using a ratio of dye monomer to DMAEMA of 5:95 by weight, giving dye polymer DP3, and a ratio of dye monomer to DMAEMA of 10:90 by weight, giving dye polymer DP4.

Example 3

Polymerisation Reactions Involving an Anionic Dye Monomer

Using procedures analogous to those detailed in Example 2, co-polymers of DMAEMA and Acid Blue 25 acrylate at 95:5 and 90:10 by weight were prepared, these dye polymers being coded DP5 and DP6, respectively.

Example 4

Polymerisation Reactions Involving a Cationic Dye Monomer

Using procedures analogous to those detailed in Example 2, co-polymers of DMAEMA and Methylene Violet 3RAX acrylate at 99:1, 98:2, 95:5 and 90:10 by weight were prepared, these dye polymers being coded DP7, DP8, DP9 and DP10 respectively.

UV-Vis Spectra of Dye Polymers

Table 1 gives details of the UV-Vis spectra of dye polymers indicated.

TABLE 1

| Dye polymer | Dye monomer | Dye content (nominal %) | $\lambda_{max}$ (nm) | Absorbance* |
|---|---|---|---|---|
| PP1 | DAQ maleate | 0.6 | 540 | 0.08 |
| PP2 | DAQ maleate | 2.4 | 540 | 0.22 |
| PP3 | DAQ maleate | 4.8 | 540 | 0.56 |
| PP4 | DAQ maleate | 9.6 | 540 | 0.67 |
| DP2 | DAQ acrylate | 1 | 541 | 0.08 |
| DP3 | DAQ acrylate | 5 | 544 | 0.72 |
| DP4 | DAQ acrylate | 10 | 546 | 1.10 |

TABLE 1-continued

| Dye polymer | Dye monomer | Dye content (nominal %) | $\lambda_{max}$ (nm) | Absorbance* |
|---|---|---|---|---|
| DP5 | Acid Blue 25 acrylate | 5 | 551 | 0.76 |
| DP6 | Acid Blue 25 acrylate | 10 | 534 | 1.37 |
| DP7 | Methylene Violet 3RAX acrylate | 1 | 557 | 0.45 |
| DP8 | Methylene Violet 3RAX acrylate | 2 | 557 | 1.29 |
| DP9 | Methylene Violet 3RAX acrylate | 5 | 557 | 2.31 |
| DP10 | Methylene Violet 3RAX acrylate | 10 | 557 | 4.47 |

*1 cm cell, 1 g/L*. DP5 and DP6 in 0.1% aqueous linear alkylbenzenesulphonate solution, others in water.

Dye Polymer Deposition Experiments

Extracted human incisors and premolars were pre-cleaned by brushing with a white silica paste and placed in sterile saliva for 2 hours to allow a pellicle to form. The teeth were then placed in a test solution of the dye polymer (0.1% by weight) for 1 min. static soak. Excess solution was removed by dabbing the side of the tooth on absorbent tissue. The colour of the teeth was measured before and after treatment using a chromameter. Table 2 gives the results in terms of CIE $\Delta b^*$, where $\Delta b^* = b^*$(after treatment)$-b^*$(before treatment). Negative values indicate deposition of the dye polymer and hence enhanced whiteness of the tooth. The results are each averages of results from six teeth.

TABLE 2

| Dye Polymer | $\Delta b^*$ |
|---|---|
| Control (water) | 0.02 |
| PP2 | −0.3 |
| PP3 | −0.4 |
| PP4 | −0.5 |
| DP2 | −0.12 |
| DP3 | −0.37 |
| DP4 | −0.50 |
| DP5 | −0.32 |
| DP6 | −0.54 |
| DP7 | −0.4 |
| DP8 | −0.9 |
| DP9 | −1.4 |
| DP10 | −2.5 |

These results indicate that the dye polymers deposit effectively onto the teeth and enhance their whiteness.

Example 4

Oral Care Compositions

The compositions detailed in Table 3 may be prepared by methods known in the art.

TABLE 3

| Ingredient | % |
|---|---|
| Fine ground natural chalk | 40.00 |
| Sorbitol (70% aq) | 15.00 |
| Thickening silica | 3.00 |
| Sodium carboxymethyl cellulose | 0.90 |
| flavour | 1.10 |
| sweetner | 0.23 |
| Sodium lauryl sulphate | 2.50 |
| glycine | 3.60 |
| NaOH | 1.0 |
| formalin | 0.1 |
| Sodium monofluorophosphate | 1.0 |
| Trisodium phosphare | 0.5 |
| Dye polymer | 0.1 |
| water | To 100 |

The invention claimed is:

1. An oral care composition comprising water, thickener, surfactant, abrasive, and a dye polymer;
    wherein the dye polymer is of the form:
    (Polymer chain)-(Y-dye)$_x$
    wherein Y is a link between the dye and the polymer chain and x is a number of dye moieties associated with a polymer molecule;
    wherein Y is an organic bridging group covalently connecting an aromatic ring of a dye moiety to a polymer chain;
    wherein Y has from 1 to 8 atoms wherein the atoms are selected from the group consisting of C, N, O, S, and combinations thereof;
    wherein the dye polymer has a hue angle of from 220 to 320 degrees;
    and wherein a water solubility of the dye polymer is at least 0.01 grams per liter at 25 degrees Celsius; and
    wherein the oral care composition comprises 0.05 wt % to 0.5 wt % of the dye polymer based a total weight of the oral care composition;
    wherein the oral care composition does not include a deposition aid;
    and wherein said oral care composition comprises a visually distinct core formulation located coaxially with a visually distinct sheath formulation.

2. An oral care composition according to claim 1, wherein the dye polymer comprises anthraquinone moieties.

3. An oral care composition according to claim 1, wherein the dye polymer has a number average molecular weight in the range from 2500 to 250000.

4. An oral care composition according to claim 1, wherein the dye polymer has a molar ratio of dye moieties to polymerized monomer units in the polymer chain of from 1:100 to 1:5.

* * * * *